United States Patent

Brimhall et al.

[11] Patent Number: 6,090,074
[45] Date of Patent: Jul. 18, 2000

[54] ECCENTRIC ROTARY HIGH PRESSURE SEAL

[75] Inventors: Greg L. Brimhall, West Jordan; Stephen Lynn Thoresen, Orem, both of Utah

[73] Assignee: Becton, Dickinson and Company, Franklin Lakes, N.J.

[21] Appl. No.: 09/185,274

[22] Filed: Nov. 3, 1998

Related U.S. Application Data

[62] Division of application No. 08/935,409, Sep. 23, 1997, abandoned.

[51] Int. Cl.[7] .................................................. A61M 5/178
[52] U.S. Cl. ............................. 604/167.05; 604/167.01; 604/248
[58] Field of Search .................................. 604/167, 169, 604/246, 248, 256

[56] References Cited

U.S. PATENT DOCUMENTS

| | | | |
|---|---|---|---|
| 4,735,614 | 4/1988 | Yapp et al. | 604/165 |
| 4,931,044 | 6/1990 | Beiter | 604/248 |
| 5,084,023 | 1/1992 | Lemieux | 604/167 |
| 5,403,284 | 4/1995 | Gross | 604/167 |
| 5,498,247 | 3/1996 | Brimhall | 604/244 |
| 5,582,597 | 12/1996 | Brimhall et al. | 604/192 |
| 5,584,810 | 12/1996 | Brimhall | 604/110 |
| 5,725,506 | 3/1998 | Freeman et al. | 604/169 |

FOREIGN PATENT DOCUMENTS 2 088 215  11/1984  United Kingdom .

*Primary Examiner*—Corrine McDermott
*Attorney, Agent, or Firm*—Eric M. Lee

[57] ABSTRACT

An eccentric rotary high pressure seal is disclosed herein. This seal includes a valve body and a spring located in a housing. The spring biases the valve body to rotate. The valve body defines a longitudinally extending passage having dimensions sufficient to allow an introducer needle to pass there through. This passage is offset from the axis of the valve body. The valve body is located in a housing that will allow the valve body to rotate therein. The housing defines two longitudinally aligned openings that are offset from the axis of the housing. These two longitudinally aligned openings are oriented such that the passage in the valve body can be aligned with the openings located in the housing. In this manner, an introducer needle can extend into the housing and hold the valve body against the bias of the spring. Once the introducer needle is removed from the housing, the valve body is no longer held in place against the force of the spring. Therefore, the spring causes the valve body to rotate within the housing so that the passage in the valve body is not aligned with the two longitudinally aligned openings formed in the housing. This prevents fluid flow through the housing past the valve body once the introducer needle is removed therefrom.

4 Claims, 9 Drawing Sheets

ECCENTRIC ROTARY HIGH PRESSURE SEAL

This application is a divisional of application Ser. No. 08/935,409 filed Sep. 23, 1997, now abandoned.

BACKGROUND OF THE INVENTION

The present invention relates to a seal for use with a medical device such as a catheter and introducer needle assembly. Although this invention has particular applicability to a catheter and introducer needle assembly, it is to be understood that the seal of this invention may be used in connection with other devices requiring a fluid seal as well.

Catheters, particularly intravenous (IV) catheters, are used for directing fluid into or withdrawing fluid from a patient. The most common type of IV catheter is an over the needle catheter. As its name implies, an over the needle catheter is mounted over an introducer needle having a sharp distal tip. With the distal tip of the introducer needle extending beyond the distal tip of the catheter, the assembly is inserted through the patient's skin into a blood vessel. Once placement of the assembly in the blood vessel is verified by flashback of blood in the needle and into a flashback chamber located at the proximal end of the needle, the needle is withdrawn leaving the catheter in place.

In standard catheters, the proximal end of the catheter typically has a hub, through which the introducer needle extends, that is designed to be connectable to a fluid supply line after insertion of the catheter in a patient and removal of the introducer needle. When the introducer needle is removed from the catheter and before the fluid supply line is connected to the catheter hub, there is nothing blocking the flow of fluid into or out of the patient through the catheter. And since the catheter is located in a patient's blood vessel, blood can flow out of the catheter and contaminate the clinician as well as other personnel and medical supplies that happen to be in the area. Similarly, where a catheter with a side port is used, blood can flow out of the proximal end of the catheter hub through the portion where the introducer needle was located even when a fluid supply line is connected to the side port before the introducer needle is removed.

In recent years there has been increasing need for catheters that eliminate or at least limit the amount of blood leakage therefrom. This need has arisen because of the advent of currently incurable and sometimes fatal diseases, such as hepatitis and acquired immunodeficiency syndrome ("AIDS"), which can be transmitted by the exchange of body fluids from an infected person to another person. As a result of this need, some catheters have been designed to include some type of seal in the portion of the catheter hub through which the introducer needle extends to minimize blood leakage through the catheter hub once the catheter has been properly placed in a patient's blood vessel and the introducer needle has been removed. Typical seals merely comprise an elastic plug located in the catheter hub. This allows the introducer needle to extend through the plug and to be subsequently removed from the plug once the catheter is properly in place in a blood vessel. Since the plug is elastic, the plug should reseal once the needle is removed from the seal. Unfortunately such seals in these prior devices may be inadequate.

For example, the elastic plug tends to take a set around the introducer needle during the time that the catheter and introducer needle assembly is shipped to a customer and held in inventory prior to use. This is particularly problematic where large gauge introducer needles are used. Once the introducer needle is removed, instead of the plug sealing the opening left by the needle, the opening remains in the plug. This opening provides a path for blood flow out of the catheter. In addition, such an opening provides a path for infection to enter the patient's blood stream. Moreover, such elastic plug seals are not particularly effective in preventing leakage in high pressure locations.

SUMMARY OF THE INVENTION

It is therefore an object of this invention to provide a seal that will prevent fluid flow there through.

It is another object of this invention to provide a seal for use in a catheter and introducer needle assembly where the seal will not take a set around the introducer needle even where the introducer needle is located in the seal for a prolonged period of time and where a large gauge introducer needle is used.

It is yet another object of this invention to provide a seal that will prevent fluid flow there through even in high pressure locations.

The eccentric rotary high pressure seal of this invention includes a valve body and a rotary biasing mechanism such as a spring. The valve body defines a longitudinally extending passage having dimensions sufficient to allow an introducer needle to pass there through. This passage is offset from the axis of the valve body, the relevance of which will be described hereinafter. The valve body is located in a housing that allows the valve body to rotate therein. The housing defines two longitudinally aligned openings that are offset from the axis of the housing. These two longitudinally aligned openings are oriented such that the passage in the valve body can be aligned with the openings located in the housing. In this manner, an introducer needle can extend into the housing through one end, through the valve body and past the other end of the housing.

The spring is located in the housing with respect to the valve body to bias the valve body in a particular rotary orientation. Specifically, the spring is located about the valve body so it can rotate the valve body to move the passage out of alignment with the two longitudinally aligned openings formed in the housing. With the introducer needle extending into the housing and through the valve body, the valve body is held in place against the force of the spring by the introducer needle. Once the introducer needle is removed from the housing and the valve body, the valve body is no longer held in place against the force of the spring. Therefore, the spring causes the valve body to rotate within the housing so that the passage in the valve body is no longer aligned with the two longitudinally aligned openings formed in the housing. This prevents fluid flow through the housing past the valve body.

One end of the valve body is formed with a larger surface area than the other end of the valve body. When fluid flows against the end of the valve body with the larger surface area a high pressure is exerted against that end of the valve body. This forces the other end of the valve body tightly against the housing to ensure a fluid tight seal. Thus leakage through the housing and the valve body is minimized.

The above and other objects and advantages of the invention will be apparent upon consideration of the following detailed description.

BRIEF DESCRIPTION OF THE DRAWINGS

The preferred embodiments are illustrated in the drawings in which like reference numerals refer to like elements and in which.

DETAILED DESCRIPTION OF THE INVENTION

As used herein, the term "proximal" refers to a location on the eccentric rotary high pressure seal of this invention closest to the clinician using the eccentric rotary high pressure seal and farthest from the patient in connection with whom the eccentric rotary high pressure seal is used. Conversely, the term "distal" refers to a location on the eccentric rotary high pressure seal of this invention farthest from the clinician using the eccentric rotary high pressure seal and closest to the patient in connection with whom the eccentric rotary high pressure seal is used.

The eccentric rotary high pressure seal of this invention is described hereinafter in connection with a particular configuration of a catheter and introducer needle assembly. This description provides a frame of reference for the location and use of the eccentric rotary high pressure seal of this invention. However, it is to be understood that the eccentric rotary high pressure seal of this invention is not limited in its application to the particular configuration of the catheter and introducer needle assembly described herein. Indeed, the eccentric rotary high pressure seal of this invention is not even limited to a catheter and introducer needle assembly but may be used in other applications where a high pressure fluid seal is needed.

Figure 1:
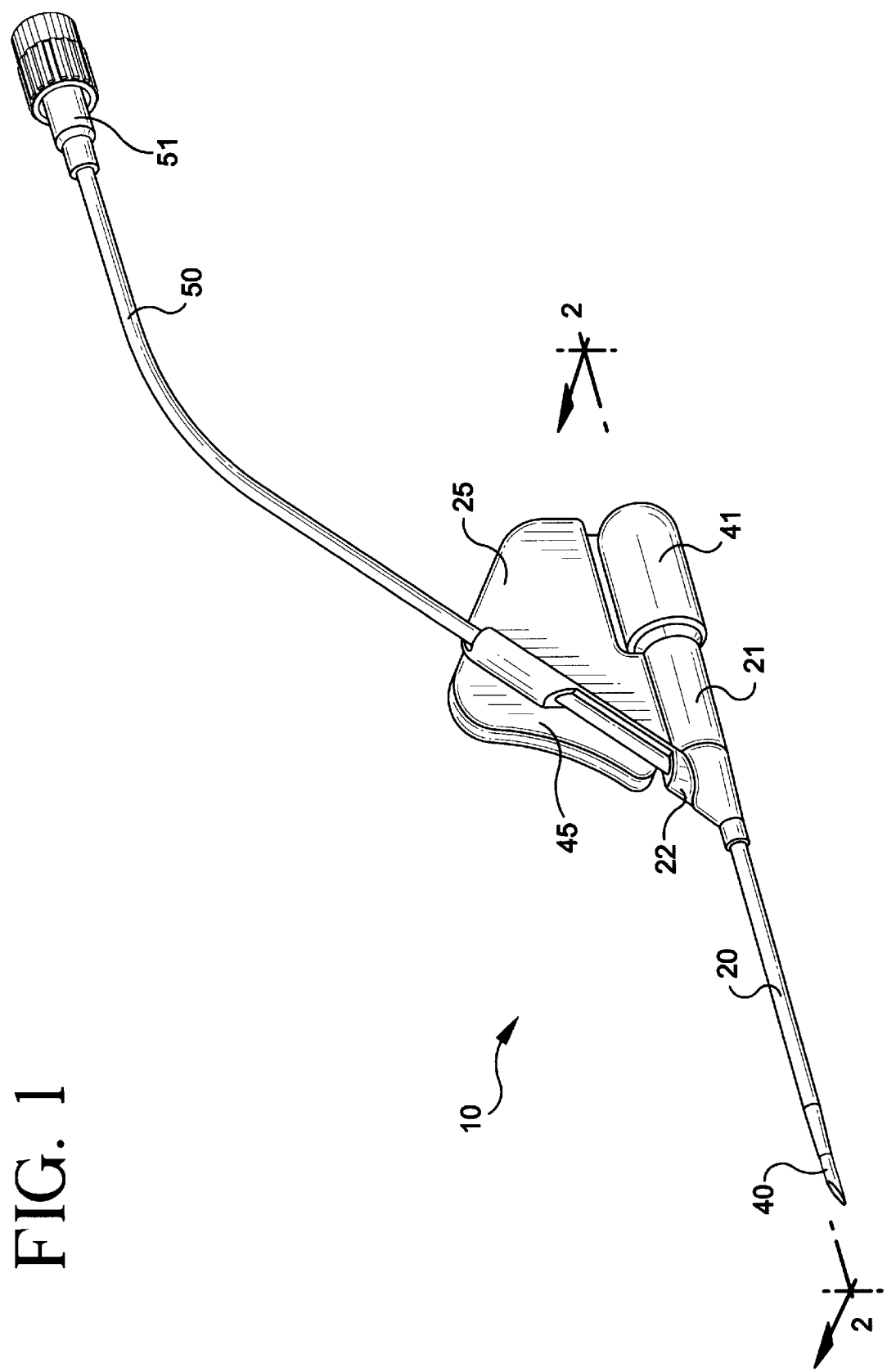
FIG. 1 is a perspective view of a catheter and introducer needle assembly that includes the eccentric rotary high pressure seal of this invention.
Figure 2:
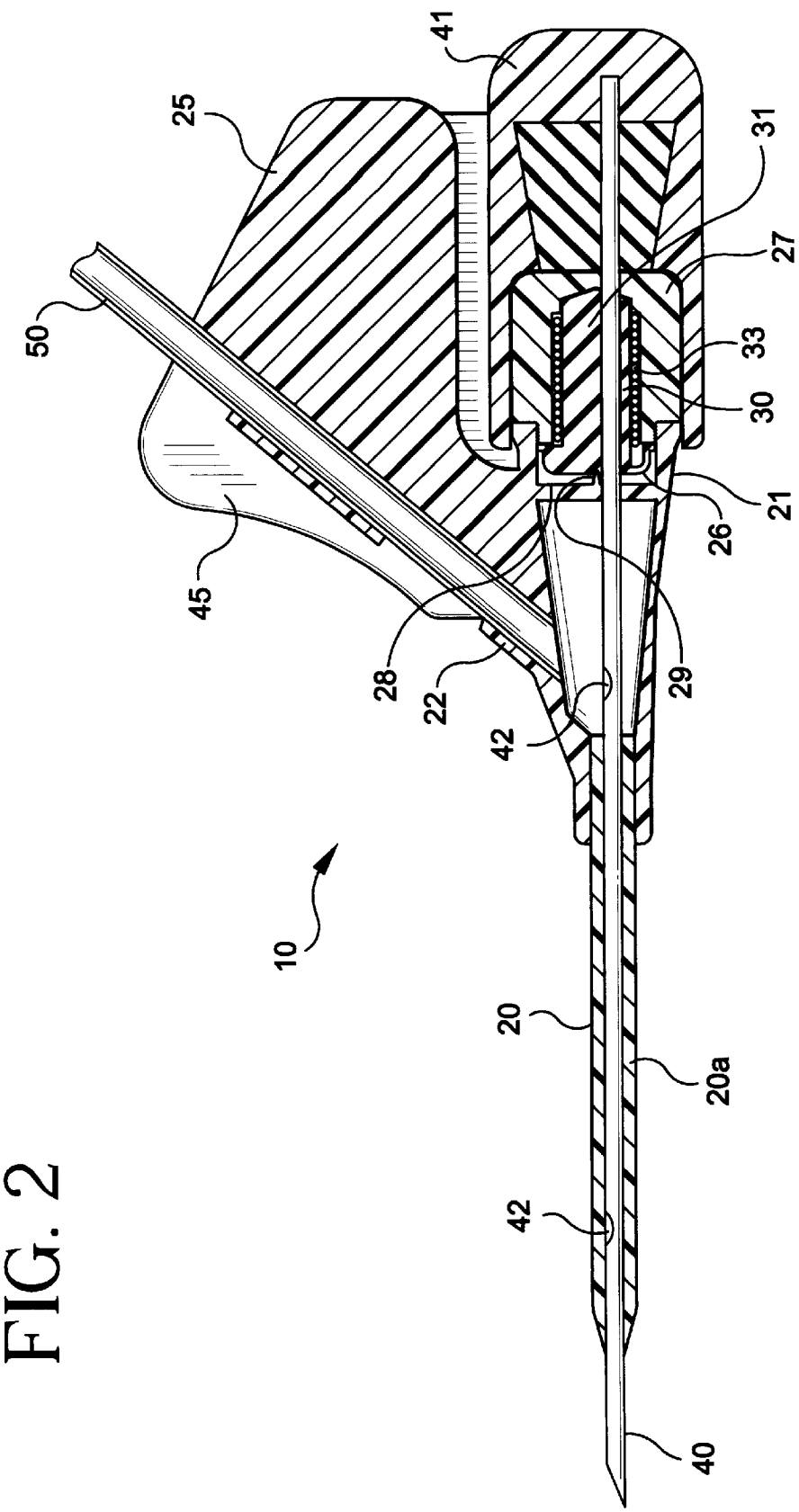
FIG. 2 is a partial cross sectional view of the catheter and introducer needle assembly of FIG. 1 taken along line 2—2 that includes the eccentric rotary high pressure seal of this invention.

The catheter and introducer needle assembly 10 depicted in FIGS. 1 and 2 includes a catheter 20 having its proximal end affixed to the distal end of a catheter hub 21 and a needle 40 having its proximal end affixed to the distal end of a needle hub 41. Needle 40 is disposed in catheter 20 so that catheter hub 21 and needle hub 41 are abutting and the distal end of needle 40 extends beyond the distal end of catheter 20. The eccentric rotary high pressure seal 30 of this invention is located in and is formed as a part of catheter hub 21.

Catheter hub 21 includes a side port 22 which has an extension tube 50 connected thereto located toward the distal portion of catheter hub 21. Catheter hub 21 also includes a wing 25 that extends radially from catheter hub 21. Wing 25 is generally aligned with the longitudinal axis of catheter 20. Wing 25 should be large enough to be grasped easily by a clinician to facilitate manipulation of catheter and introducer needle assembly 10 during venipuncture.

The proximal end of extension tube 50 includes a standard luer lock adapter 51 to allow the connection of an IV fluid supply line to extension tube 50. Such an IV fluid supply line can be connected to extension tube 50 prior to insertion of the distal portion of catheter and introducer needle assembly 10 into a patient. Side port 22 is in fluid communication with the lumen of catheter 20 so that fluid infused through extension tube 50 will pass into the patient once catheter 20 is properly placed in the patient and needle 40 is removed from catheter and introducer needle assembly 10. Conversely, blood exiting a patient's vein through catheter 20 can travel through extension tube 50. Catheter hub 21 is sealed with eccentric rotary high pressure seal 30 to ensure that fluid such as blood does not leak out of the proximal end of catheter hub 21 but instead travels through extension tube 50.

Eccentric rotary high pressure seal 30 includes a valve body 31 and a rotary biasing mechanism such as a spring 33. Of course, other rotary biasing mechanisms such as elastic tubes could be used in place of spring 33. Valve body 31 defines a longitudinally extending passage 32 having dimensions sufficient to allow needle 40 to pass there through. Passage 32 is offset from the axis of valve body 31. The distal end of valve body 31 is preferably formed with an enlarged shoulder portion 35 having a larger distal surface area than the proximal end of valve body 31.

Valve body 31 is preferably enclosed in a proximal compartment 26 of catheter hub 21. Proximal compartment 26 is defined by proximal portion 27 and distal wall 28 and provides sufficient space for valve body 31 to rotate therein. A spindle 29 is located on distal wall 28 and provides a centering mechanism around which valve body 31 can rotate. If desired, the inner proximal end of proximal portion 27 can define a saucer-shaped depression 23 to provide a second centering mechanism around which valve body 31 can rotate. Such a second centering mechanism ensures that valve body 31 will rotate around its axis without wobbling during the rotation. Proximal compartment 26 may also be formed with a radially inwardly extending tab 39 that engages another radially outwardly extending tab 35a formed on shoulder portion 35. Preferably tab 35a extends over about one half of the circumference of shoulder portion 35 to maintain proper alignment and smooth rotation of valve body 31. These tabs limit the amount of rotation of valve body 31 in proximal compartment 26.

Figure 3:
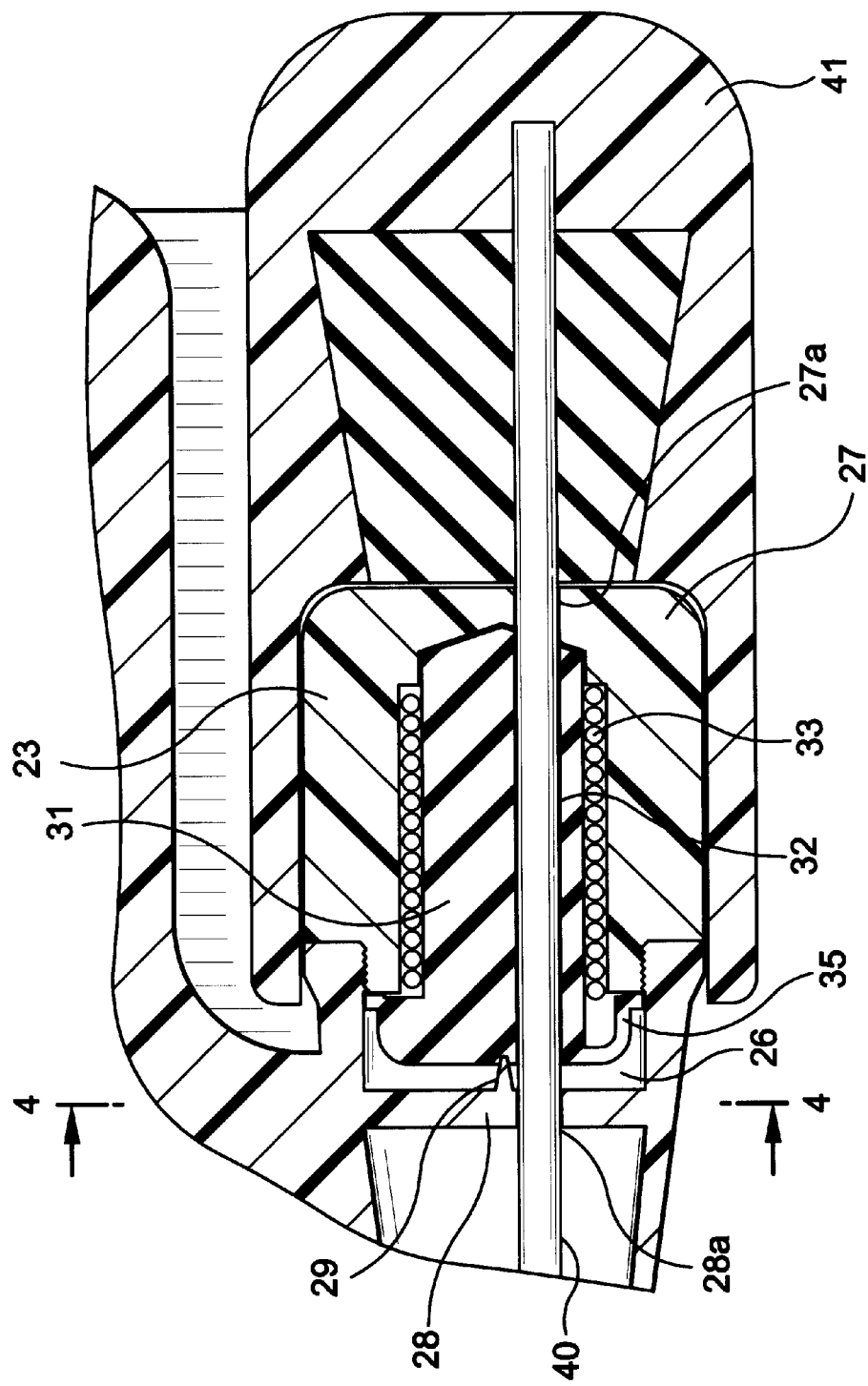
FIG. 3 is an enlarged cross sectional view of the proximal portion of the catheter and introducer needle assembly of FIG. 1 to show the eccentric rotary high pressure seal of this invention with the introducer needle extending therethrough.
Figure 4:
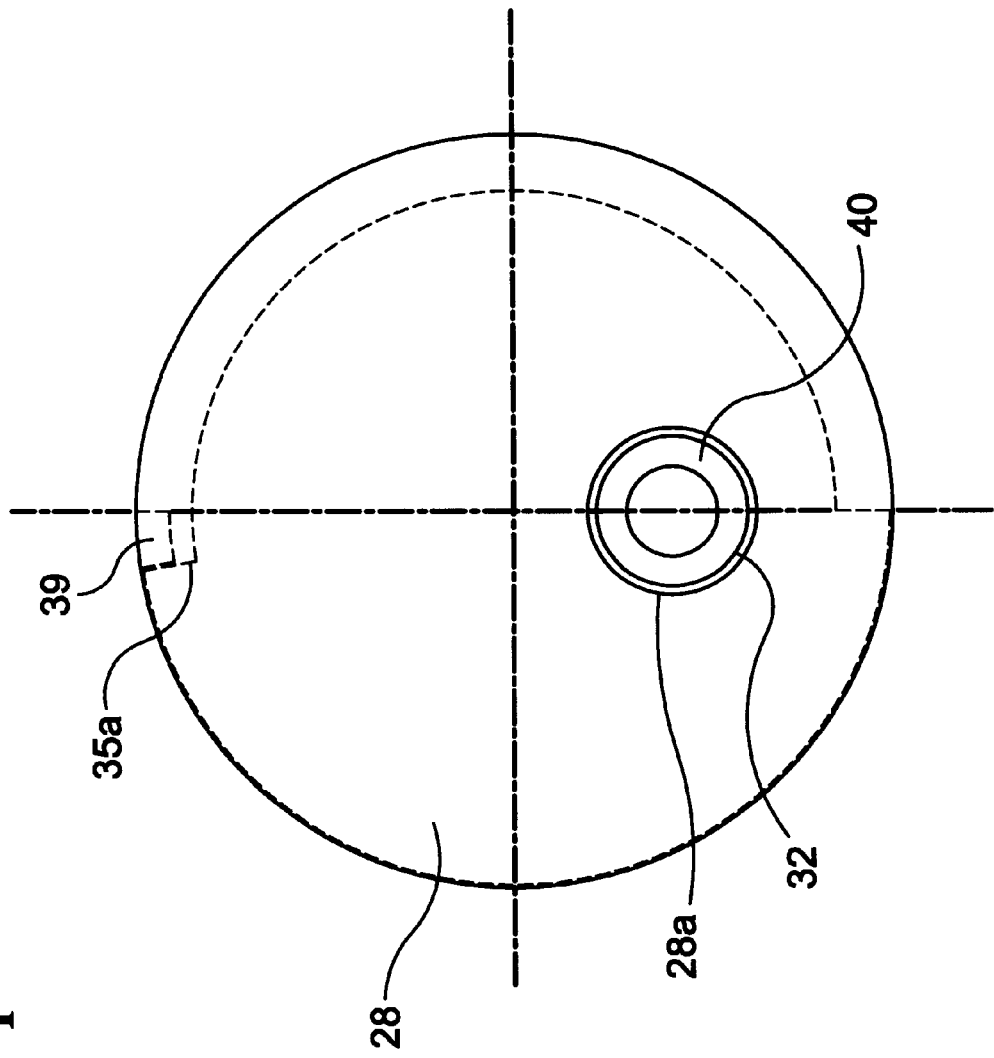
FIG. 4 is a schematic cross sectional view of the proximal portion of the catheter and introducer needle assembly taken along line 4—4 of FIG. 3 showing the distal face of the distal wall used in the catheter hub that forms a portion of the housing for the rotary high pressure seal of this invention.

Distal wall 28 defines a distal opening 28a that is longitudinally aligned with the lumen 20a of catheter 20. Proximal portion 27 defines a proximal opening 27a that is longitudinally aligned with distal opening 28a. This configuration allows needle 40 to extend into catheter hub 21, catheter 20 and catheter lumen 20a through valve body 31 when passage 32 is aligned with proximal opening 27a and distal opening 28a. See FIGS. 3 and 4.

Figure 5:
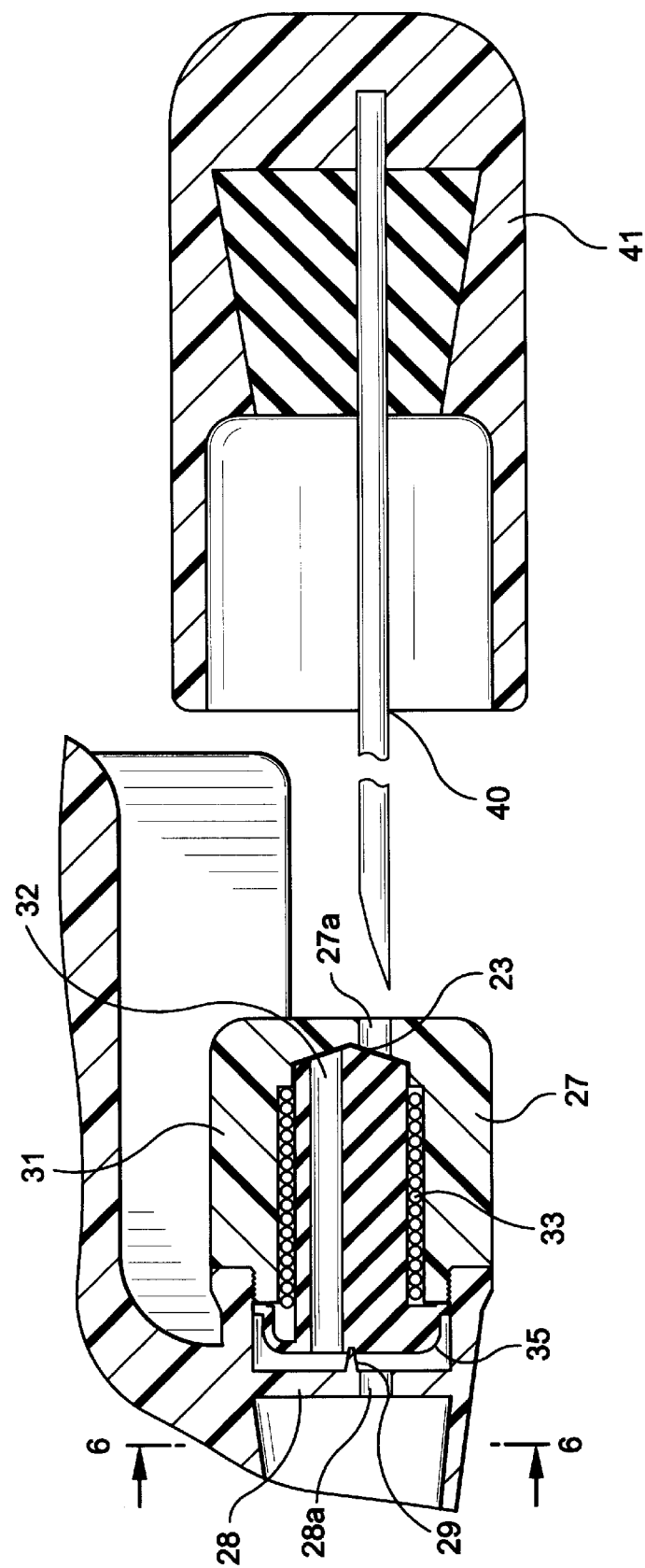
FIG. 5 is an enlarged cross sectional view of the proximal portion of the catheter and introducer needle assembly of FIG. 1 with the catheter and the introducer needle separated to show the eccentric rotary high pressure seal of this invention in the orientation when the introducer needle has been removed therefrom.
Figure 6:
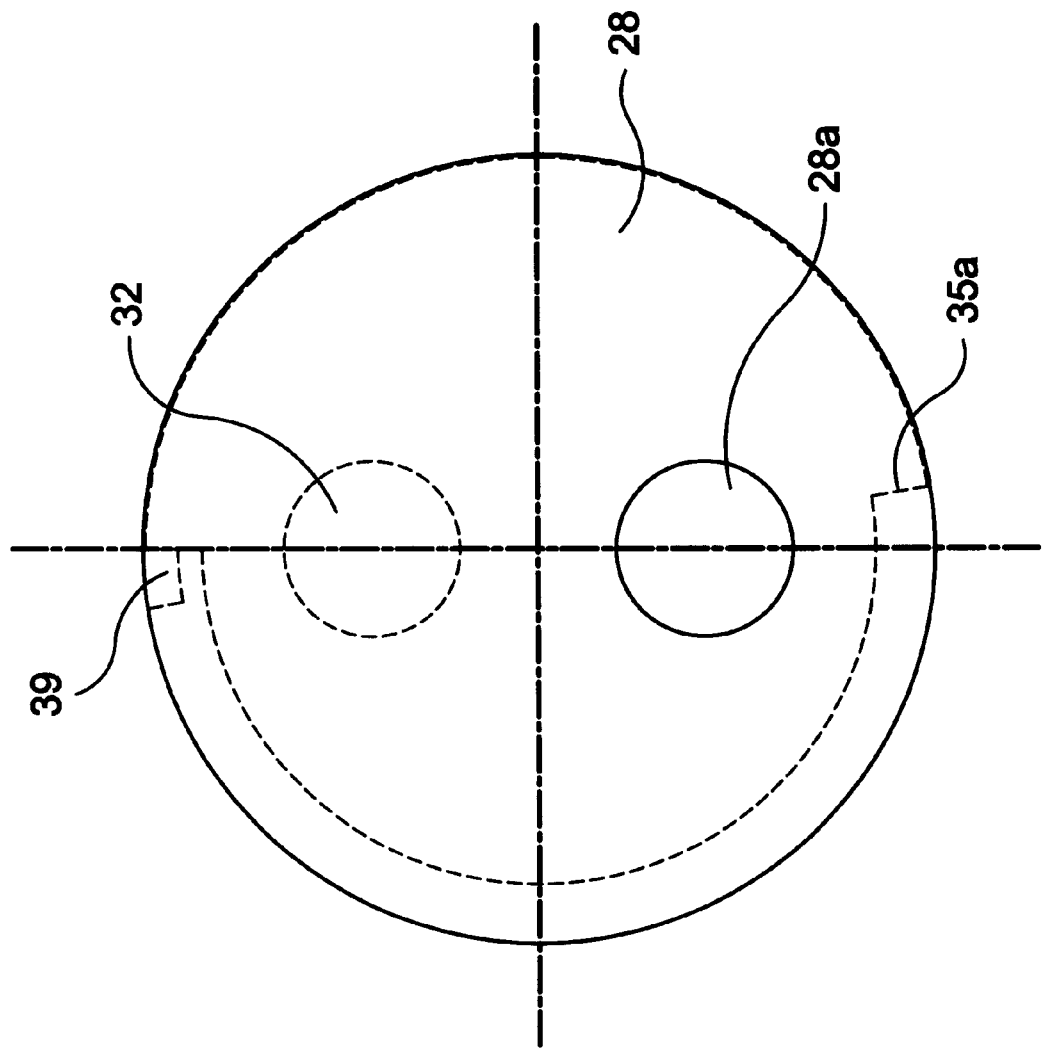
FIG. 6 is a schematic cross sectional view of the proximal portion of the catheter and introducer needle assembly taken along line 6—6 of FIG. 5 showing the distal face of the distal wall used in the catheter hub that forms a portion of the housing for the rotary high pressure seal of this invention.

Spring 33 is located in proximal compartment 26 with respect to valve body 31 to bias valve body 31 in a rotary motion. Specifically, spring 33 is located about and contacts valve body 31 in such a manner so as to rotate valve body 31 about spindle 29 and depression 23 so that passage 32 is not aligned with proximal opening 27a and distal opening 28a. This misalignment of proximal opening 27a and distal opening 28a with passage 32 occurs in the unbiased state of valve body 31 and spring 33. In order to align proximal opening 27a and distal opening 28a with passage 32, valve body 31 must be rotated against the force of spring 33. This rotation results in rotary energy stored in spring 33 to bias valve body 31 toward its misalignment position. When needle 40 extends into catheter hub 21 and through proximal opening 27a, distal opening 28a and valve body 31, valve body 31 is held in place against the force of spring 33 by needle 40. See FIGS. 3 and 4. Once needle 40 is removed from catheter hub 21 and valve body 31, valve body 31 is no longer held in place against the force of spring 33. Therefore, spring 33 causes valve body 31 to rotate within catheter hub 21 so that passage 32 is not aligned with proximal opening 27a and distal opening 28a. See FIGS. 5 and 6.

As discussed above, tabs 35a and 39 may also be used to prevent over rotation of valve body 31 by spring 33. By having a slight biasing force by spring 33 urge tabs 35a and 39 together, misalignment between proximal opening 27a and distal opening 28a with passage 32 is ensured.

Figure 7:
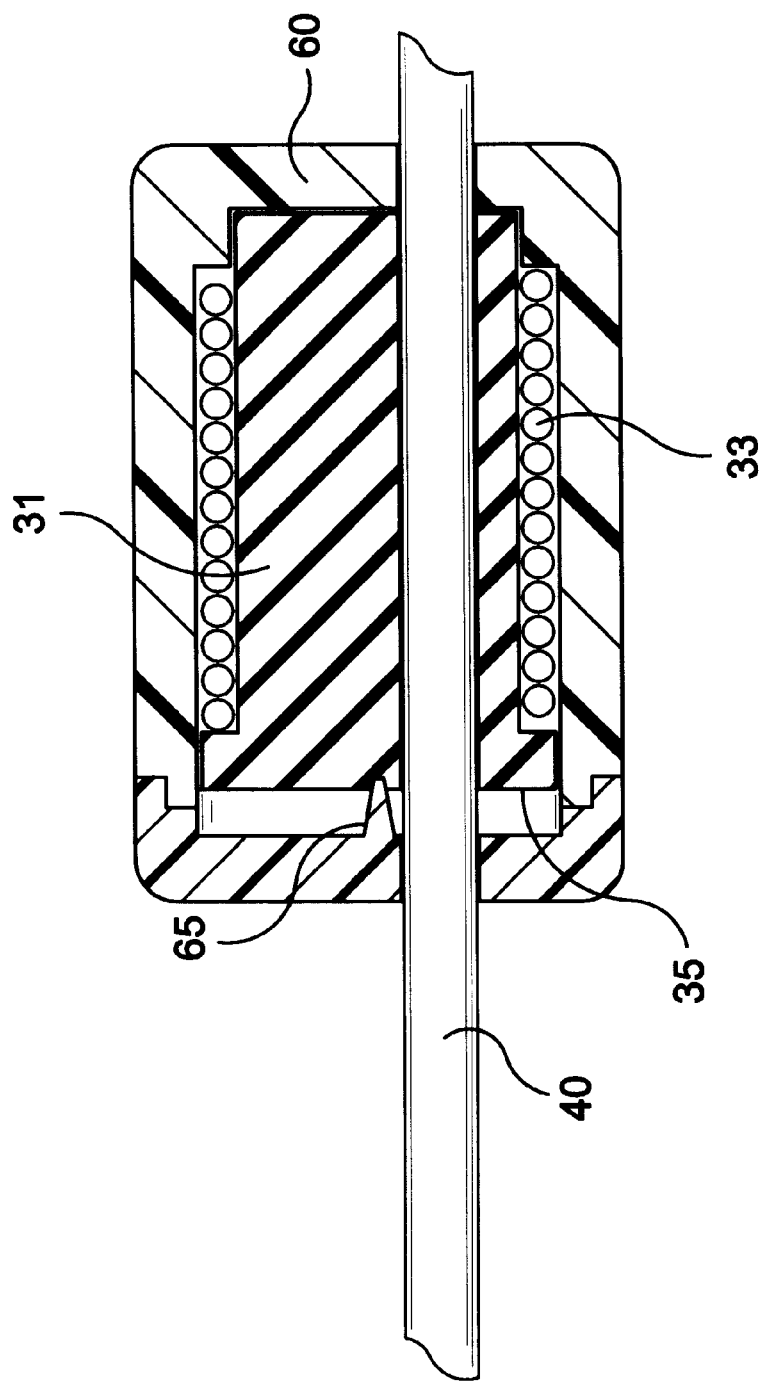
FIG. 7 is a cross sectional view of the eccentric rotary high pressure seal of this invention in a separate housing apart from a catheter showing a portion of a needle extending therethrough.
Figure 8:
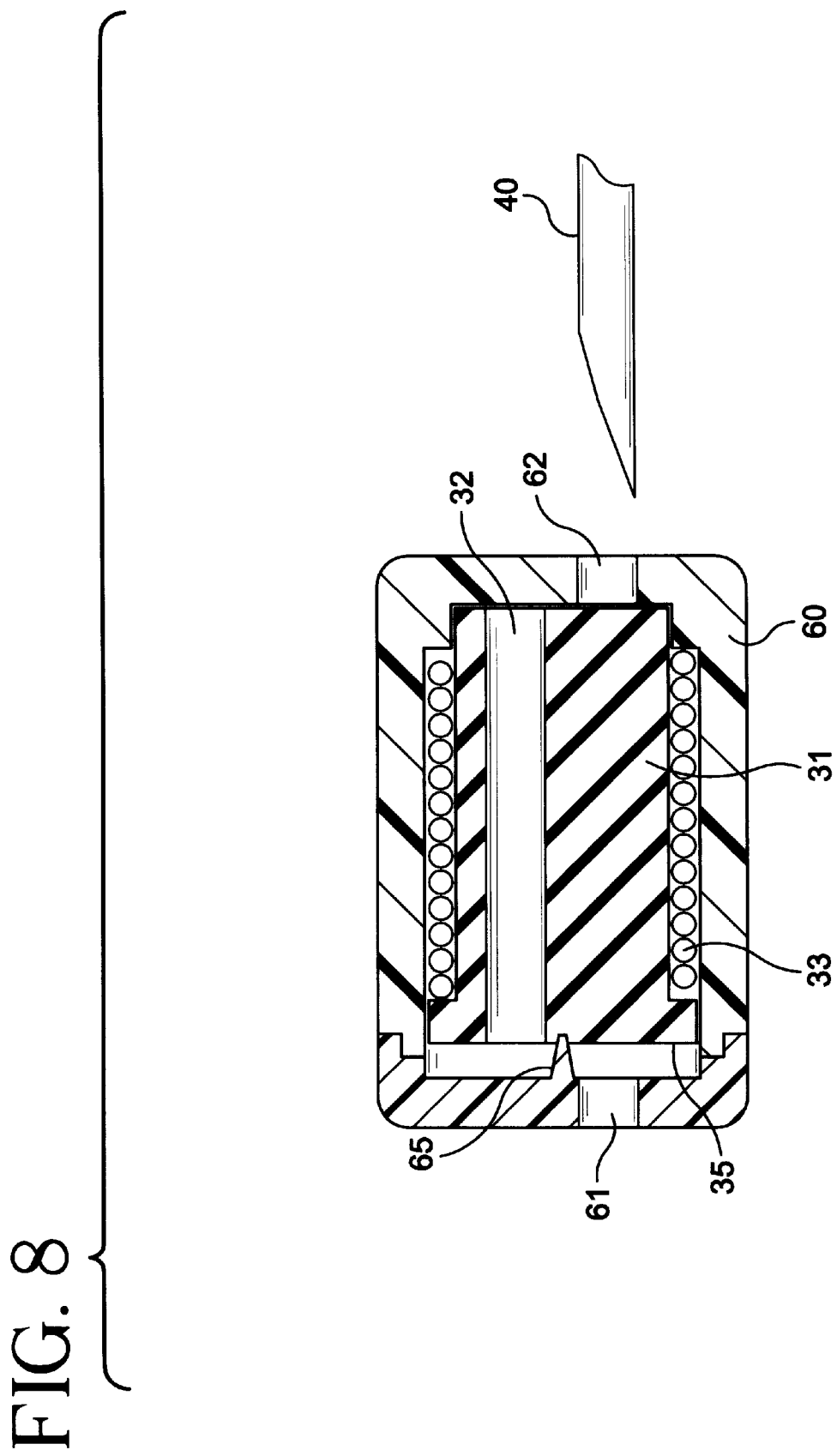
FIG. 8 is a cross sectional view of the eccentric rotary high pressure seal of this invention in a separate housing apart from a catheter with the needle removed therefrom.
Figure 9:
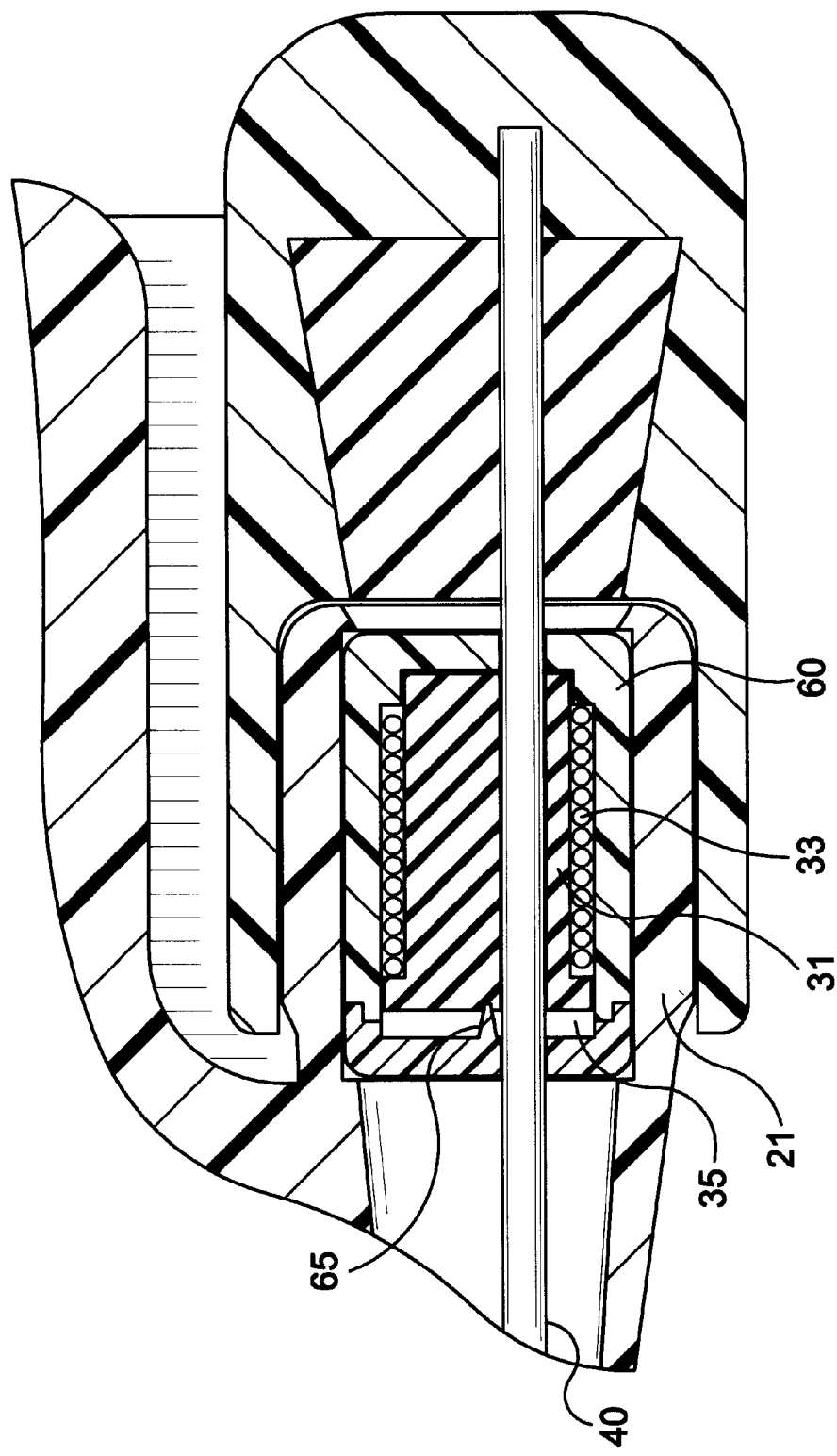
FIG. 9 is an enlarged cross sectional view of the proximal portion of the catheter and introducer needle assembly showing the eccentric rotary high pressure seal of this invention formed with a separate housing snapped into place in the catheter hub.

In an alternate embodiment, valve body 31 is longitudinally restrained in a separate housing 60 which can be snapped into place in the proximal end of catheter hub 21. See FIG. 9. In this configuration, a pair of longitudinally aligned openings 61 and 62 are located in housing 60 and are offset from the axis of housing 60. Openings 61 and 62 are oriented such that passage 32 in valve body 31 can be aligned therewith when valve body 31 is in a particular rotary alignment in housing 60. See FIGS. 7 and 9. In this manner, needle 40 can extend into housing 60 and through valve body 31. As in the other embodiment, a rotary biasing mechanism such as a spring 33 is located in housing 60 to bias valve body 31 toward the misaligned configuration where openings 61 and 62 and passage 32 are not aligned. When needle 40 extends into housing 60, valve body 31 is held in place against the force of spring 33 by needle 40. See FIGS. 7 and 9. Once needle 40 is removed from housing 60, valve body 31 is no longer held in place against the force of spring 33. Therefore, spring 33 causes valve body 31 to rotate within housing 60 about spindle 65 so that passage 32 is not aligned with openings 61 and 62. Again tabs may be formed in housing 60 and valve body 31 to prevent over rotation of valve body 31 by spring 33.

The misalignment of passage 32 and the openings into catheter hub 21, or housing 60, prevents fluid flow past valve body 31. When fluid flows against shoulder portion 35 of valve body 31, the force exerted against shoulder portion 35 is higher than the force that would be exerted against the proximal end of valve body 31 if fluid were to flow into the space between the proximal end of valve body 31 and the proximal wall of housing 60. This is because the magnitude of the force is directly related to the surface area against which the pressure is exerted. Thus where the same pressure is exerted against a larger surface area the force will be greater than where that same pressure is exerted against a smaller surface area. Since the surface area of the proximal end of valve body 31 is smaller than the surface area of shoulder 35, a higher force is exerted against shoulder 35. This higher force ensures that the proximal end of valve body 31 is tightly abutted against the proximal wall of housing 60. A fluid tight seal between the proximal end of valve body 31 and the proximal wall of housing 60 results. Thus leakage through housing 60 and valve body 31 is minimized. Although the distal end of valve body 31, i.e. shoulder 35, is described herein as having a larger surface area than the proximal end of valve body 31 it is to be understood that the proximal end of valve body 31 can have a larger surface area than the distal end of valve body 31 if fluid flow past valve body 31 is from the proximal end toward the distal end.

Needle 40 has its proximal end connected to needle hub 41. Radially extending fin 45 is formed on needle hub 41 and is generally longitudinally aligned with needle 40. Fin 45 in combination with wing 25 facilitates manipulation of catheter and introducer needle assembly 10 during venipuncture. In addition, fin 45 facilitates removal of needle 40 from catheter 20 after a successful venipuncture. Needle 40 may include one or more notches 42 formed along a distal portion thereof. Such notches allow blood to flow out of needle 40 into the annular space between needle 40 and catheter 20 where it can be observed by a clinician as long as catheter 20 is at least translucent. Alternatively, blood could flow into extension tube 50 where it would be observed by a clinician as long as extension tube 50 is at least translucent. If notches 42 are not formed in needle 40, a flashback chamber (not shown) could be located in needle hub 41 at the proximal end of needle 40. In such a configuration, a clinician could observe blood flow into the flashback chamber at the proximal end of catheter and introducer needle assembly 10. It is important to be able to observe blood flow into catheter and introducer needle assembly 10 because the observation of blood therein confirms that the distal end of catheter and introducer needle assembly 10 is properly located in a patient's blood vessel.

To use catheter and introducer needle assembly 10 with eccentric rotary high pressure rotary seal 30 of this invention, the clinician would take catheter and introducer needle assembly 10 in the orientation shown in FIG. 1. In this orientation, needle 40 extends into catheter 20 through valve body 31 such that the distal end of needle 40 extends distally past the distal end of catheter 20. The clinician can then proceed to perform a venipuncture with the distal end of catheter 20 and needle 40. Once a successful venipuncture has been made, blood will flow into needle 40 and through notches 42. Blood will then flow into the annular space between needle 40 and catheter 20 and into extension tube 50. The clinician will be able to observe this flow of blood to confirm the successful venipuncture. At this point, the clinician can advance catheter 20 further into the vein and simultaneously remove needle 40 from catheter 20. Once the distal end of needle 40 is completely removed from catheter and introducer needle assembly 10, spring 33 forces valve body 31 to rotate so as to misalign passage 32 with proximal opening 27a and distal opening 28a. This prevents any blood flow out of the proximal end of catheter hub 21. If the blood is at a high pressure, the blood will press against the distal end of valve body 31 with greater force to ensure a fluid tight seal between valve body 31 and proximal wall 27.

Thus it is seen that an eccentric rotary high pressure seal is provided that will prevent fluid flow there through, that may be used in a catheter and introducer needle assembly and that will not take a set around the introducer needle even where the introducer needle is located in the seal for a prolonged period of time and where a large gauge introducer needle is used and that will prevent fluid flow there through even in high pressure locations.

We claim:

1. A catheter and introducer needle assembly, comprising;

a catheter having a proximal end and a distal end;

a catheter hub connected to the proximal end of the catheter and in fluid communication with the catheter, the catheter hub having a proximal wall defining a proximal opening and a distal wall defining a distal opening;

a valve body having a distal face and a proximal face disposed in the catheter hub for rotary movement therein, the valve body defining a longitudinally extending passage therethrough which may be aligned with the proximal opening and the distal opening in a particular rotary orientation;

a rotary biasing mechanism disposed in the catheter hub and in contact with the valve body;

an introducer needle having a proximal end and a distal end disposed inside the catheter and the catheter hub through the passage and the proximal opening and the distal opening;

a needle hub having a proximal end and a distal end connected to the proximal end of the needle; and a first tab radially extending from the valve body and a second tab located in the catheter hub to prevent over rotation of the valve body with respect to the catheter hub under the force of the rotary biasing mechanism.

2. A catheter and introducer needle assembly, comprising;

a catheter having a proximal end and a distal end;

a catheter hub connected to the proximal end of the catheter and in fluid communication with the catheter, the catheter hub having a proximal wall defining a proximal opening and a distal wall defining a distal opening;

a valve body having a distal face and a proximal face disposed in the catheter hub for rotary movement therein, the valve body defining a longitudinally extending passage therethrough which may be aligned with the proximal opening and the distal opening in a particular rotary orientation a rotary biasing mechanism disposed in the catheter hub and in contact with the valve body wherein the rotary biasing mechanism is a spring that rotates the valve body from a first position where the first opening and the second opening are aligned with the longitudinally extending passage to a second position where the first opening and the second opening are not aligned with the longitudinally extending passage;

an introducer needle having a proximal end and a distal end disposed inside the catheter and the catheter hub through the passage and the proximal opening and the distal opening;

a needle hub having a proximal end and a distal end connected to the proximal end of the needle; and a first tab radially extending from the valve body and a second tab located in the catheter hub to prevent over rotation of the valve body with respect to the catheter hub under the force of the rotary biasing mechanism.

3. A catheter and introducer needle assembly, comprising:

a catheter having a proximal end and a distal end;

a catheter hub connected to the proximal end of the catheter and in fluid communication with the catheter, the catheter hub having a proximal wall defining a proximal opening and a distal wall defining a distal opening;

a valve body having a distal face and a proximal face disposed in the catheter hub for rotary movement therein, the valve body defining a longitudinally extending passage therethrough which may be aligned with the proximal opening and the distal opening in a particular rotary orientation wherein the distal face of the valve body has a larger surface area than the proximal face;

a rotary biasing mechanism disposed in the catheter hub and in contact with the valve body;

an introducer needle having a proximal end and a distal end disposed inside the catheter and the catheter hub through the passage and the proximal opening and the distal opening;

a needle hub having a proximal end and a distal end connected to the prosimal end of the needle; and a first tab radially extending from the valve body and a second tab located in the catheter hub to prevent over rotation of the valve body with respect to the catheter hub under the force of the rotary biasing mechanism.

4. A catheter and introducer needle assembly, comprising;

a catheter having a proximal end and a distal end;

a catheter hub connected to the proximal end of the catheter and in fluid communication with the catheter, the catheter hub having a proximal wall defining a proximal opening and a distal wall defining a distal opening;

a valve body having a distal face and a proximal face disposed in the catheter hub for rotary movement therein, the valve body defining a longitudinally extending passage therethrough which may be aligned with the proximal opening and the distal opening in a particular rotary orientation wherein the distal face of the valve body has a larger surface area than the proximal face;

a rotary biasing mechanism disposed in the catheter hub and in contact with the valve body wherein the rotary biasing mechanism is a spring that rotates the valve body from a first position where the first opening and the second opening are aligned with the longitudinally extending passage to a second position where the first opening and the second opening are not aligned with the longitudinally extending passage;

an introducer needle having a proximal end and a distal end disposed inside the catheter and the catheter hub through the passage and the proximal opening and the distal opening;

a needle hub having a proximal end and a distal end connected to the proximal end of the needle; and a first tab radially extending from the valve body and a second tab located in the catheter hub to prevent over rotation of the valve body with respect to the catheter hub under the force of the rotary biasing mechanism.

* * * * *